US00PP24933P2

(12) United States Plant Patent
Ledbetter

(10) Patent No.: US PP24,933 P2
(45) Date of Patent: Sep. 30, 2014

(54) APRICOT TREE 'TWOCOT'

(50) Latin Name: ***Prunus armeniaca* L.**
Varietal Denomination: Twocot

(75) Inventor: Craig A Ledbetter, Clovis, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 66 days.

(21) Appl. No.: 13/506,771

(22) Filed: May 16, 2012

(51) Int. Cl.
*A01H 5/00* (2006.01)

(52) U.S. Cl.
USPC ..... Plt./186

(58) Field of Classification Search
USPC ..... Plt./186
See application file for complete search history.

(56) References Cited

U.S. PATENT DOCUMENTS

| | | | |
|---|---|---|---|
| PP476 | P | 6/1941 | Weschoke |
| PP503 | P | 2/1942 | Fehr |
| PP630 | P | 6/1944 | Bowers |
| PP674 | P | 4/1946 | Roberts |
| PP751 | P | 8/1947 | Heider |
| PP1,551 | P | 1/1957 | Crandall |
| PP1,651 | P | 10/1957 | Swim |
| PP1,732 | P | 7/1958 | Culbashian |
| PP2,254 | P | 4/1963 | Williams |
| PP2,255 | P | 4/1963 | Williams |
| PP2,543 | P | 7/1965 | Anderson |
| PP2,742 | P | 5/1967 | Steindorf |
| PP2,789 | P | 1/1968 | Anderson |
| PP2,826 | P | 8/1968 | Zaiger |
| PP2,906 | P | 7/1969 | Kennon |
| PP3,067 | P | 10/1971 | Hill |
| PP3,345 | P | 5/1973 | Garabedian |
| PP3,927 | P | 6/1976 | Freimann |
| PP4,339 | P | 12/1978 | Zaiger |
| PP4,553 | P | 6/1980 | Zaiger |
| PP4,673 | P | 3/1981 | Peters |
| PP5,138 | P | 11/1983 | Zaiger |
| PP5,296 | P | 10/1984 | Hemenway |
| PP5,308 | P | 10/1984 | Zaiger et al. |
| PP6,755 | P | 4/1989 | Zaiger et al. |
| PP6,923 | P | 7/1989 | Hurado et al. |
| PP7,034 | P | 9/1989 | Toyama |
| PP7,035 | P | 9/1989 | Toyama |
| PP7,045 | P | 10/1989 | Toyama |
| PP7,198 | P | 3/1990 | Zaiger et al. |
| PP7,550 | P | 6/1991 | Weinberger et al. |
| PP7,653 | P | 9/1991 | Harrison |
| PP7,917 | P | 7/1992 | Zaiger et al. |
| PP8,177 | P | 3/1993 | Corrin |
| PP8,392 | P | 9/1993 | Zaiger et al. |
| PP8,433 | P | 10/1993 | Zaiger et al. |
| PP8,674 | P | 4/1994 | Goffreda |
| PP8,932 | P | 10/1994 | Bradford et at |
| PP9,173 | P | 6/1995 | Howard |
| PP9,593 | P | 6/1996 | Zaiger et at |
| PP9,859 | P | 4/1997 | Zaiger et al. |
| PP9,864 | P | 4/1997 | Zaiger et al. |
| PP9,890 | P | 5/1997 | Ledbetter et al. |
| PP9,937 | P | 7/1997 | Zaiger et al. |
| PP10,651 | P | 10/1998 | Kovacevich |
| PP15,851 | P2 | 7/2005 | McLaren |
| PP16,119 | P2 | 11/2005 | McLaren |
| PP21,138 | P3 | 7/2010 | Maillard et al. |
| PP22,095 | P3 | 8/2011 | Holland et al. |
| 2003/0014788 | P1 | 1/2003 | Malone et al. |
| 2005/0257300 | P1 | 11/2005 | Roberts |
| 2007/0143884 | P1 | 6/2007 | Gerawan |
| 2009/0158476 | P1 | 6/2009 | Southwick et al. |
| 2009/0158477 | P1 | 6/2009 | Southwick et al. |
| 2009/0158478 | P1 | 6/2009 | Southwick et al. |
| 2009/0172847 | P1 | 7/2009 | Bradford |
| 2009/0235402 | P1 | 9/2009 | Maillard et al. |
| 2011/0030110 | P1 | 2/2011 | Holland et al. |

*Primary Examiner* — Kent L Bell
(74) *Attorney, Agent, or Firm* — John Fado; Gail E. Poulos; Lesley Shaw

(57) ABSTRACT

A new and distinct variety of apricot (*Prunus armeniaca* L.) named 'Twocot', particularly characterized by its white flesh of medium-sized fruit; upright trees with self-incompatible flowers; consistent fruit productivity during early June in California's Central San Joaquin Valley; aromatic fruit with balanced levels of sugar and fruit acid; and a late bloom interval.

14 Drawing Sheets

Latin name of the genus and species of the plant claimed: 'Twocot' is a new apricot tree that is *Prunus armeniaca* L.

Variety denomination: The new apricot tree claimed is of the cultivar denomination 'TWOCOT'.

BACKGROUND OF THE INVENTION

The present invention relates to a new and distinct variety of apricot tree, known botanically as *Prunus armeniaca* L., which has been given the variety denomination 'Twocot', as herein described and illustrated.

The new variety is a result of controlled pollination, conducted by the inventor in Fresno, Calif. The objective of the planned hybridization was to develop a new *P. armeniaca* variety having firm white flesh that would tolerate commercial manipulation during harvest and organoleptic qualities that would satisfy consumers.

The new *P. armeniaca* variety originated in 1994 when pollen from Agricultural Research Service (ARS) apricot selection P301-110 (unpatented) was applied to the unpatented seed parent New Jersey Apricot Selection No. 73 (NJA 73). Seedlings from this planned hybridization were planted at the San Joaquin Valley Agricultural Sciences Center in Parlier, Calif. The new variety 'Twocot' was discovered and selected by the inventor in 1998 as a promising seedling tree based on overall fruit quality and productivity.

The new *P. armeniaca* 'Twocot' was first asexually propagated in January 1999 by dormant grafting onto 'Nemaguard' (unpatented) peach seedling rootstocks. 'Twocot' has also been asexually reproduced by 'June-budding' of actively growing vegetative buds. Trees obtained from both methods of asexual reproduction have now produced numerous fruit crops. 'Twocot' reproduces true to type in that its unique combination of characteristics described herein remains stable and are retained through successive generations of asexual reproduction.

SUMMARY OF THE INVENTION

The following combination of traits have been observed annually on fruiting 'Twocot' trees and are determined to be unique characteristics of 'Twocot', distinguishing it as a new and distinct variety:

1. Vigorous vegetative growth on an upright to slightly spreading tree form.
2. Consistent and productive bearer of medium-sized, freestone fruit with white flesh.
3. Self-incompatible flowers that bloom late relative to other apricot cultivars grown in California.
4. Mature fruit that are aromatic and have an attractive skin blush on sun-exposed surfaces, hanging well on the tree after maturity.
5. Mid-season fruit harvest, typically during the first two weeks of June, in the Central San Joaquin Valley of California.

BRIEF DESCRIPTION OF THE PHOTOGRAPHS

The accompanying photographs illustrate the overall appearance of the new 'Twocot' apricot variety showing the colors as true as is reasonably possible with colored reproductions of this type. Colors in the photos may differ slightly from the color values cited in the detailed botanical description, which accurately describe the color of 'Twocot'.

Figure 6:
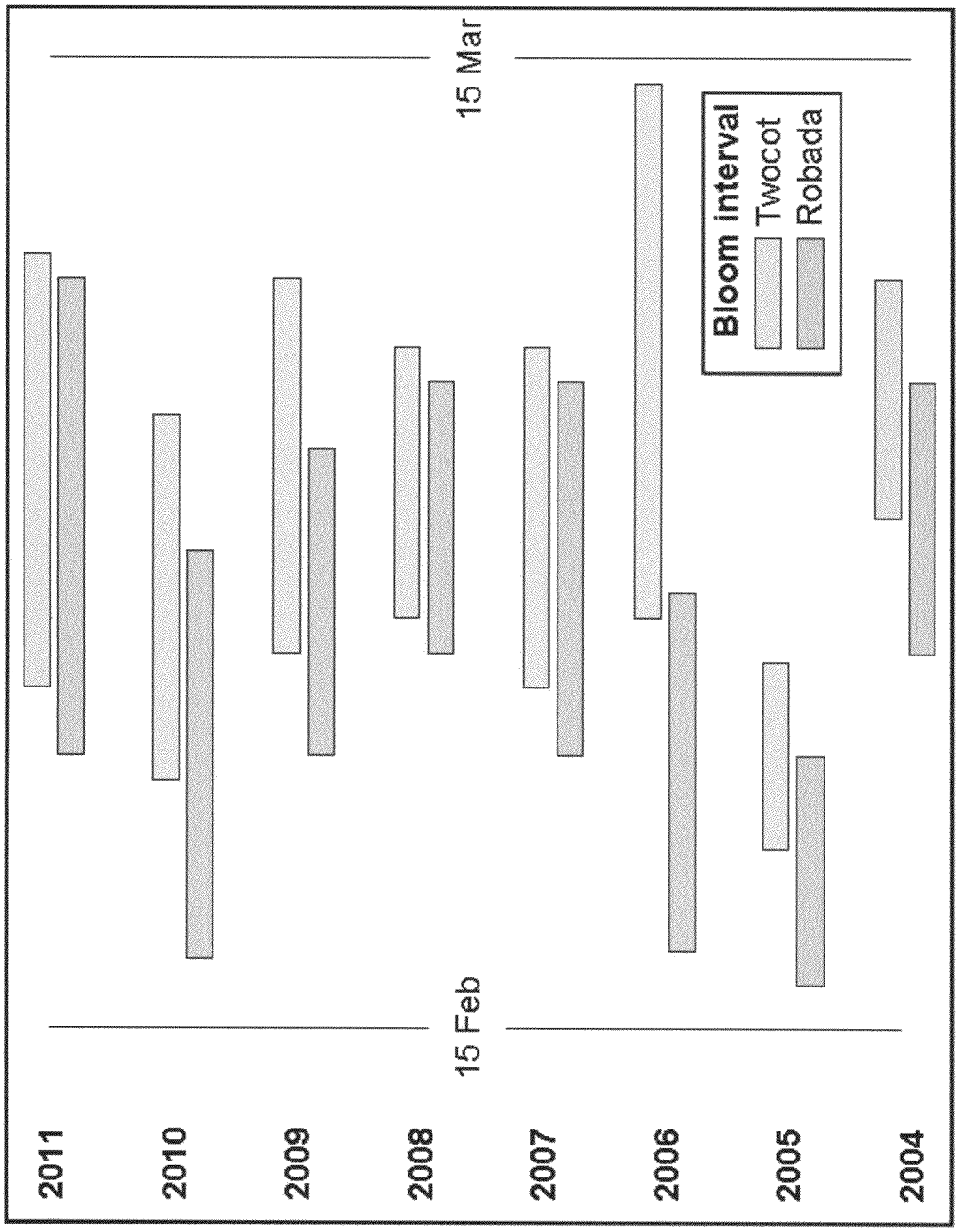

FIG. 6 is a bar graph demonstrating the degree of bloom overlap between the new variety 'Twocot' and 'Robada' (U.S. Plant Pat. No. 9,890) apricot for the harvest years 2004 through 2011 in Parlier, Calif.

Figure 7:
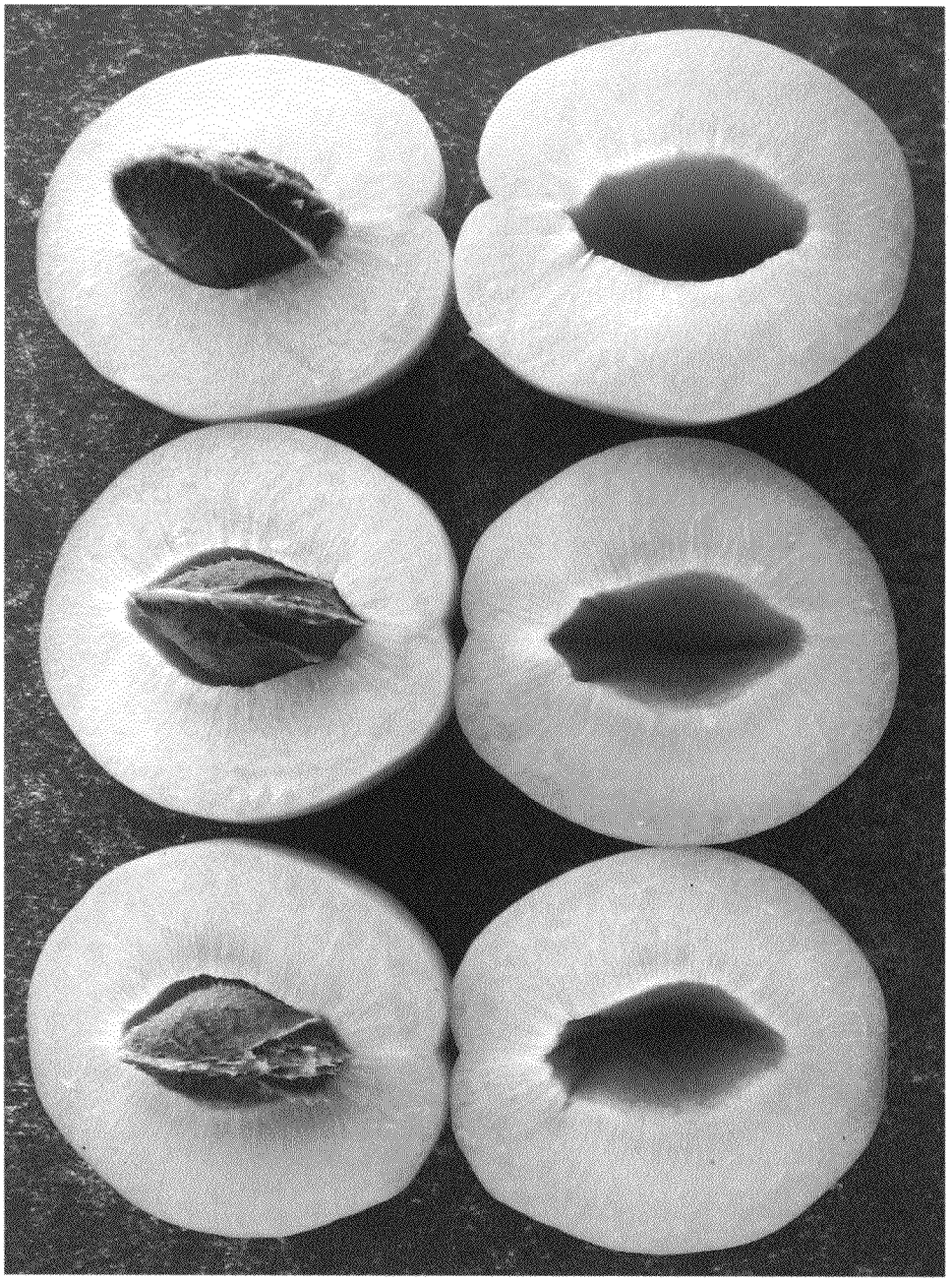

FIG. 7 is a close-up of three 'Twocot' fruit cut latitudinally in cross-section. The photograph shows the fruit form as viewed from its apex as well as the freestone nature of the new variety.

Figure 8:
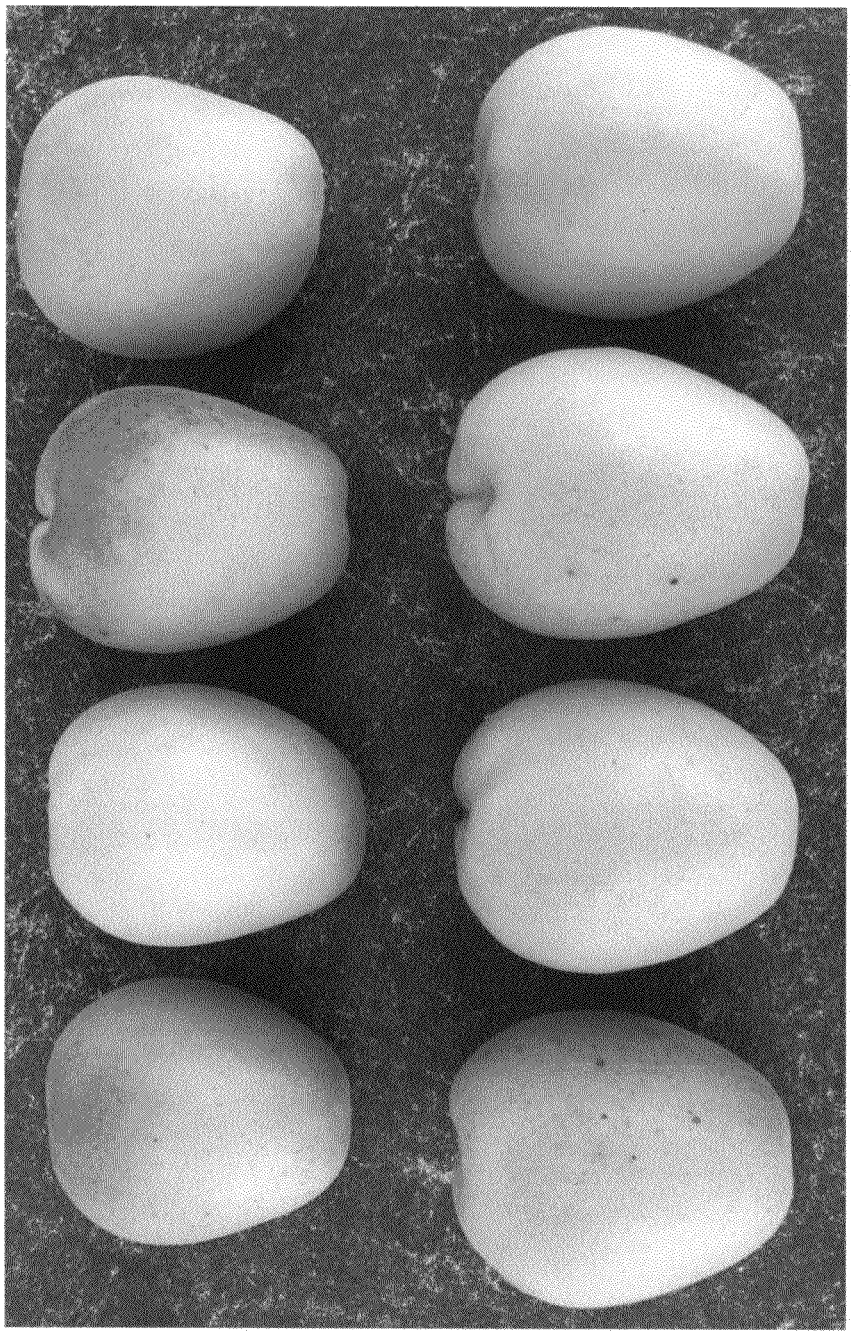

FIG. 8 shows eight 'Twocot' fruit arranged to demonstrate the fruit form as viewed perpendicular to the suture plane. Also demonstrated is the attractive skin overcolor present on sun-exposed 'Twocot' fruit.

Figure 9:
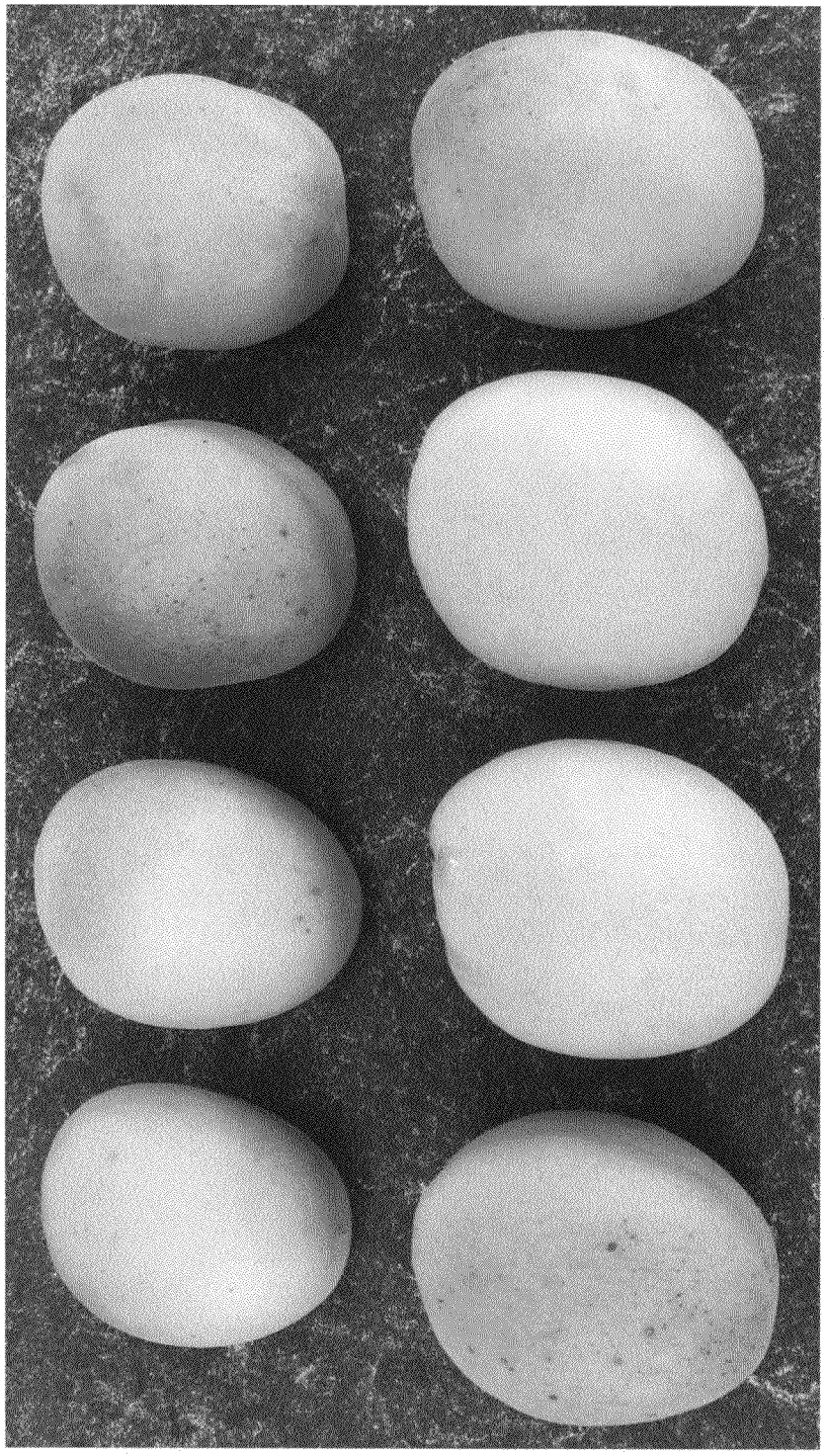

FIG. 9 shows eight 'Twocot' fruit arranged to demonstrate the fruit form as viewed in the same plane as the suture. The photo also shows skin overcolor present on some fruit.

Figure 10:
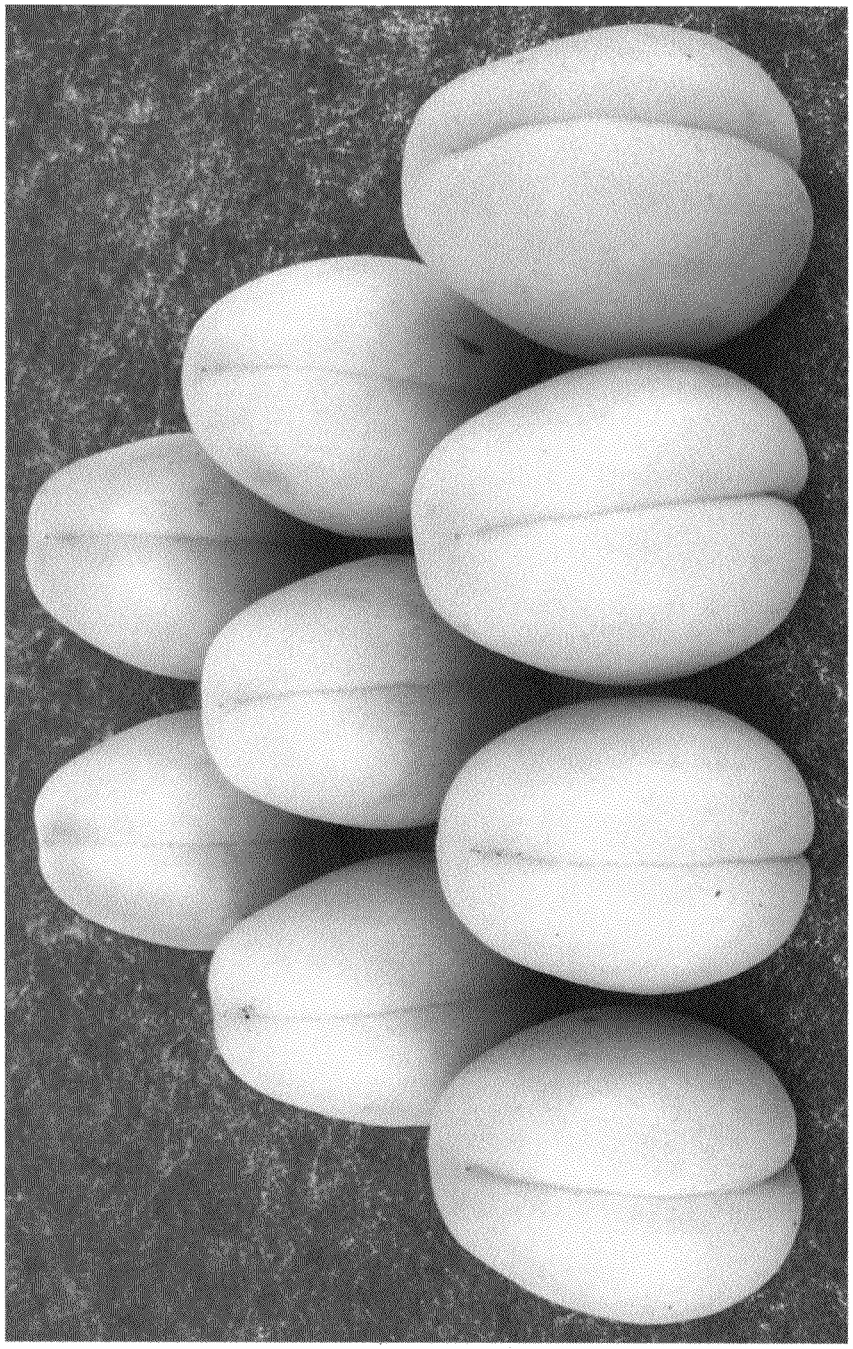

FIG. 10 shows the fruit apex shape and general suture depth of the new 'Twocot' apricot variety.

Figure 11:
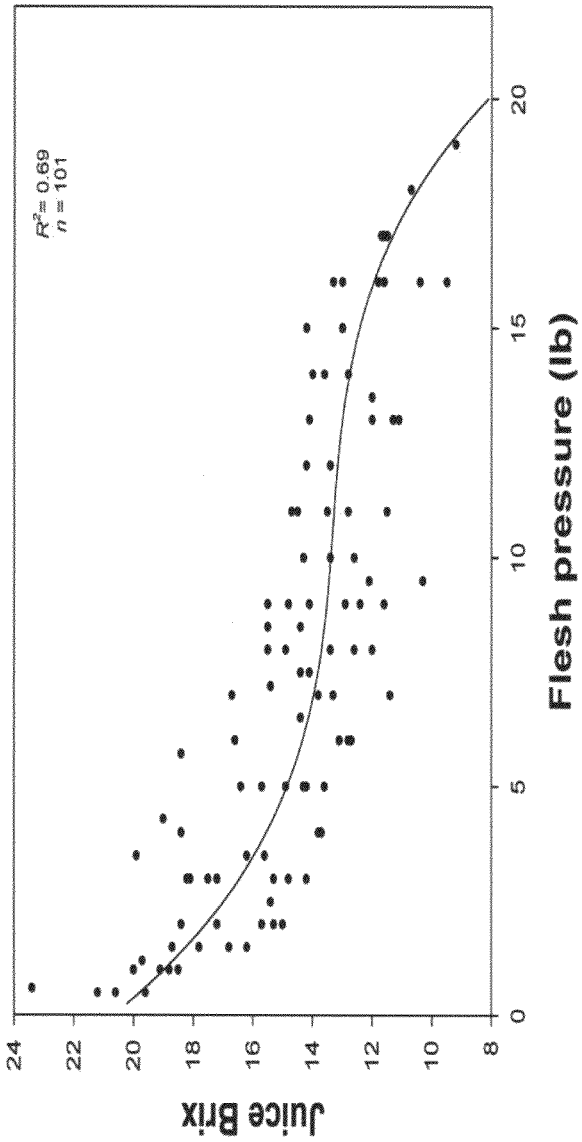

FIG. 11 is a graph demonstrating the juice Brix level of 'Twocot' fruit at various levels of flesh firmness.

Figure 12:
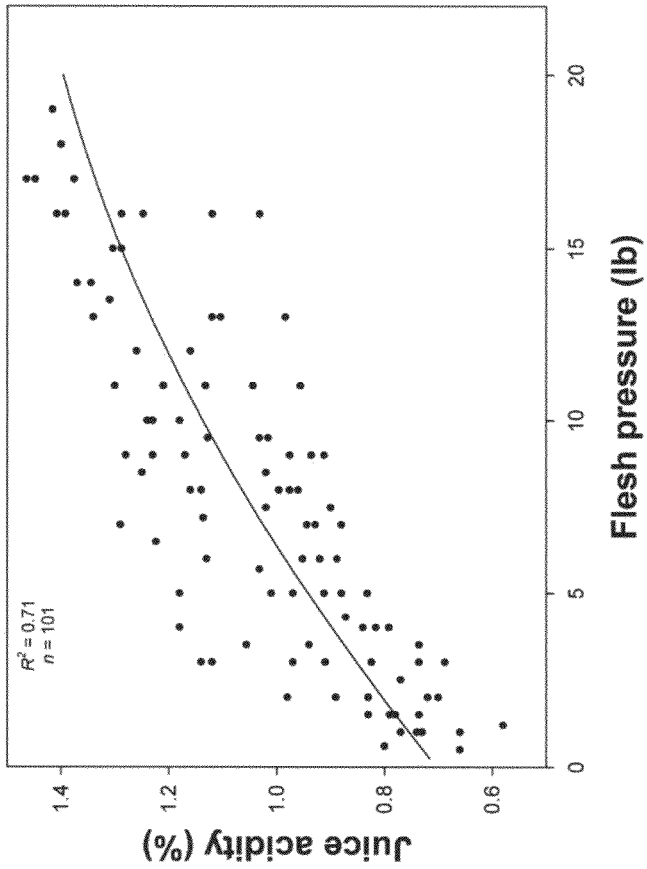

FIG. 12 is a graph demonstrating the juice acidity level of 'Twocot' fruit at various levels of flesh firmness.

Figure 13:
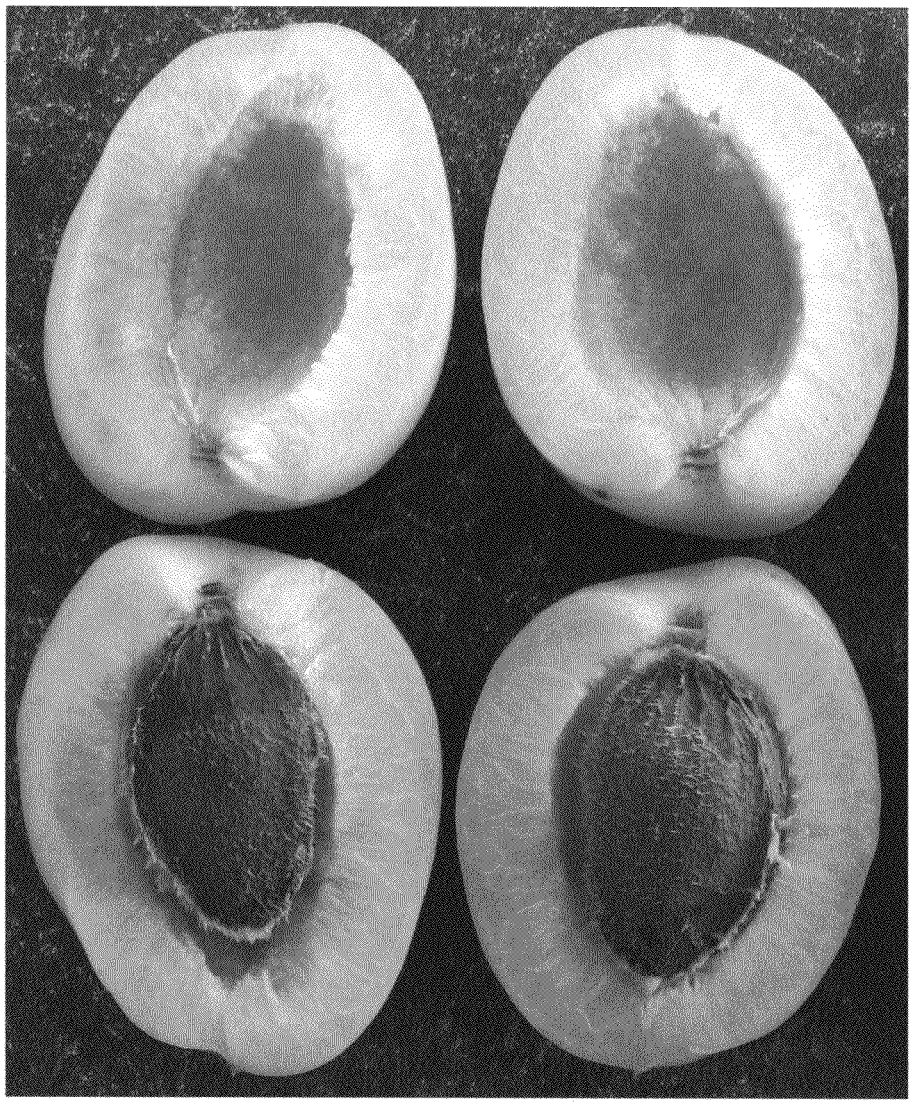

FIG. 13 shows two 'Twocot' fruit cut longitudinally in the suture plane to demonstrate the general flesh color, color of the flesh surrounding the pit and the freestone character of the new variety.

Figure 14:
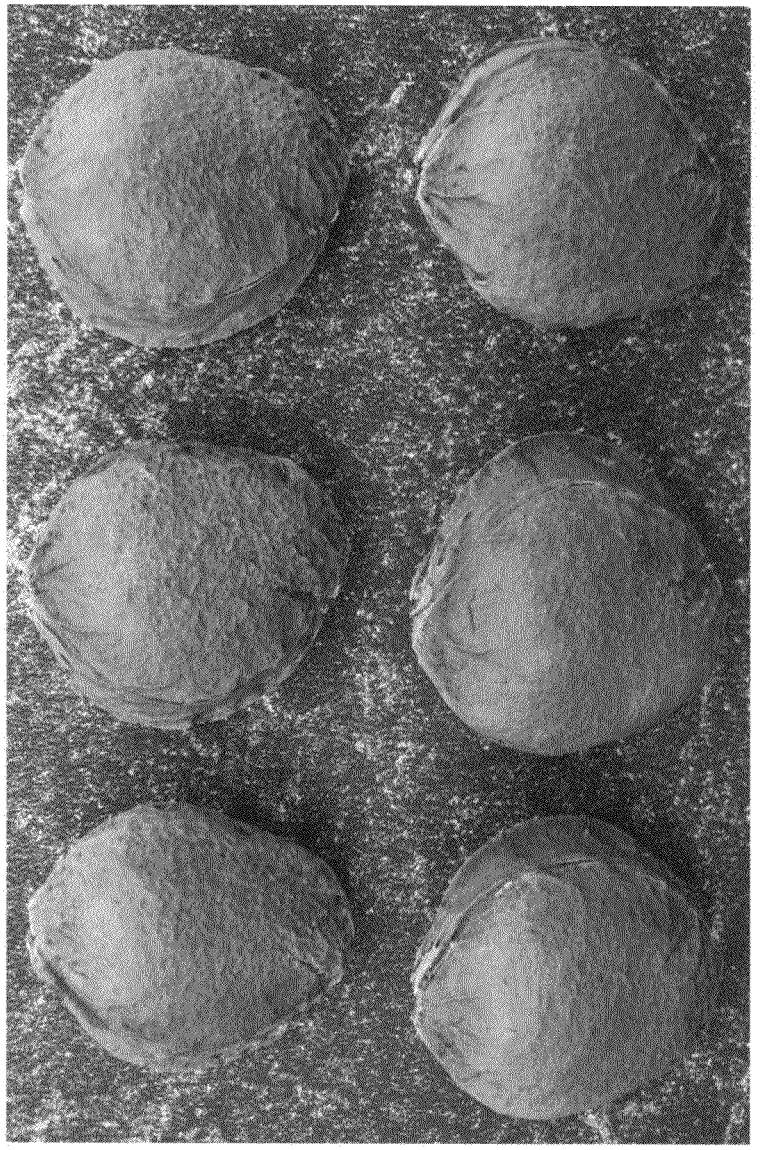

FIG. 14 shows a lateral view of six air-dried 'Twocot' stones to demonstrate the stone shape and appearance.

DETAILED DESCRIPTION OF THE INVENTION

The new 'Twocot' apricot has not been observed growing under all possible environmental conditions. The phenotype of the new variety may vary with variations in environment (chill hour accumulation, temperature extremes, light intensity, soil type & fertility, water availability) without any genotypic changes in the apricot tree.

The previously mentioned photographs along with the following measured characteristics describe the vegetative and reproductive organs of 'Twocot' apricot as grown in Parlier, Calif., under cultural conditions closely approximating those generally used in commercial apricot production. The description is believed to apply to trees of the new 'Twocot' variety grown under similar conditions of soil and climate elsewhere. However, measurements of any individual tree or group of trees of the new 'Twocot' variety may vary from the stated averages.

In a comparison with the parental accessions NJA 73 and P301-110, the new 'Twocot' variety differs primarily in the traits listed in Table 1.

TABLE 1

| TRAIT | SEED PARENT NJA 73 | NEW VARIETY 'TWOCOT' | POLLEN PARENT P301-110 |
|---|---|---|---|
| RIPENING TIME | Late June | Early June | Early May |
| BLOOM INTERVAL | Later than 'Twocot' | | Earlier than 'Twocot' |
| FLESH COLOR | White | White | Dark Orange |
| SKIN OVERCOLOR | Absent | Present (Sun Exposed) | Present (Sun Exposed) |
| FRUIT ADHESION | Well after maturity | Well after maturity | Non, falling at maturity |
| DRY FRUIT QUALITY | Poor | Excellent | Poor |

Of the many commercial apricot varieties known to the inventor, the most similar in comparison to the new variety 'Twocot' is the parental accession NJA 73, as described in the foregoing Table 1.

Pomological details of the new 'Twocot' apricot variety were collected during the 2009 and 2010 growing seasons on five and six year old trees grafted on 'Nemaguard' rootstock. Where presented numeric values are followed by a "±" in the following detailed description of 'Twocot', they represent the arithmetic mean plus or minus one standard deviation. Color code designations are provided by reference to The Royal Horticultural Society Colour Chart, The Royal Horticultural Society, London, Flower Council of Holland, Leiden, (1986). Occasionally color code designations are by reference to CIELAB color space values, and with coordinates luminosity, chroma and hue being measured with a Minolta Chroma Meter CR-200.

Tree:

*Size*.—Large. Pre-pruned dormant height of seven trees grafted on Nemaguard rootstock after nine years of growth averaged approximately 4.51 m. Canopy spread of the seven trees averaged approximately 3.05 m.

*Tree form/habit*.—Upright to slightly spreading.

*Tree vigor*.—Vigorous. Producing shoots of 1.5 to 2 m in length during the growing season.

*Tree productivity*.—Productive. Trees typically require fruit thinning to maximize fruit size.

*Bearing*.—Consistent bearing of abundant crops, does not tend to alternate bear.

Figure 1:
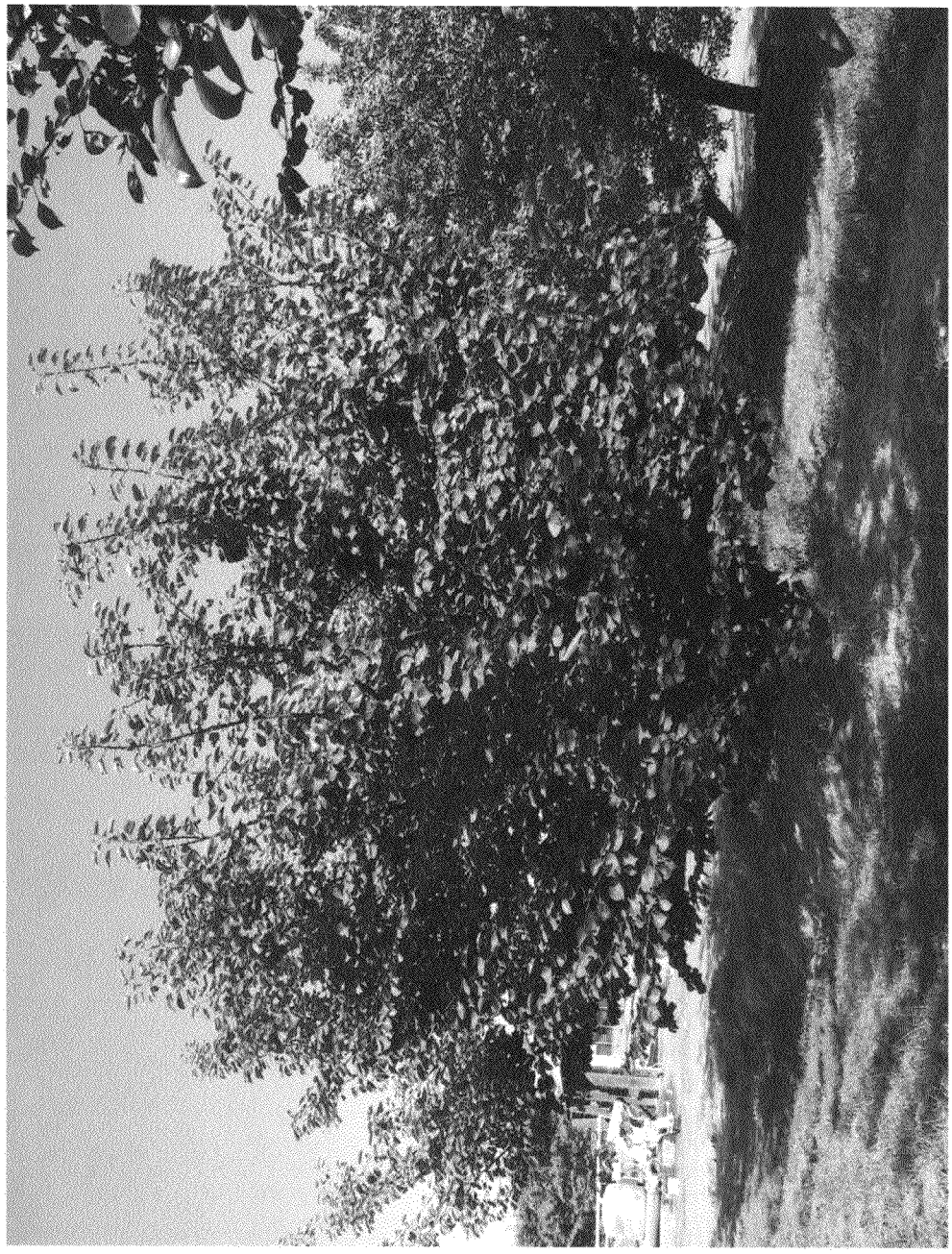
FIG. 1 shows a typical side view of a six-year old 'Twocot' tree grafted on 'Nemaguard' rootstock. The tree habit and canopy density of the new 'Twocot' apricot are demonstrated in this figure.

*Tree canopy density*.—Moderate brush density produced during growing season (FIG. 1).

*Tree hardiness*.—Demonstrated hardiness in Central San Joaquin Valley of California.

Trunk (evaluation taken 30 cm above the soil surface) and branches:

*Size*.—Average diameter of seven grafted trees in their sixth year of growth was 18.1 cm with trunks ranging from 14.3 cm to 22.9 cm.

*Texture*.—Moderate roughness to trunk bark.

*Color*.—Greyed-green (Fan 4, No. 197, B).

*Branches*.—(From 5 cm diameter branches).

*Texture*.—Generally at the transition between smooth and rougher bark development where lenticles provide a distinct tactile bump on smaller diameter branches and more splits/cracks and roughness are typical as branch diameter increases.

*Color*.—Greyed-purple (Fan 4, No. 183, B).

Figure 2:
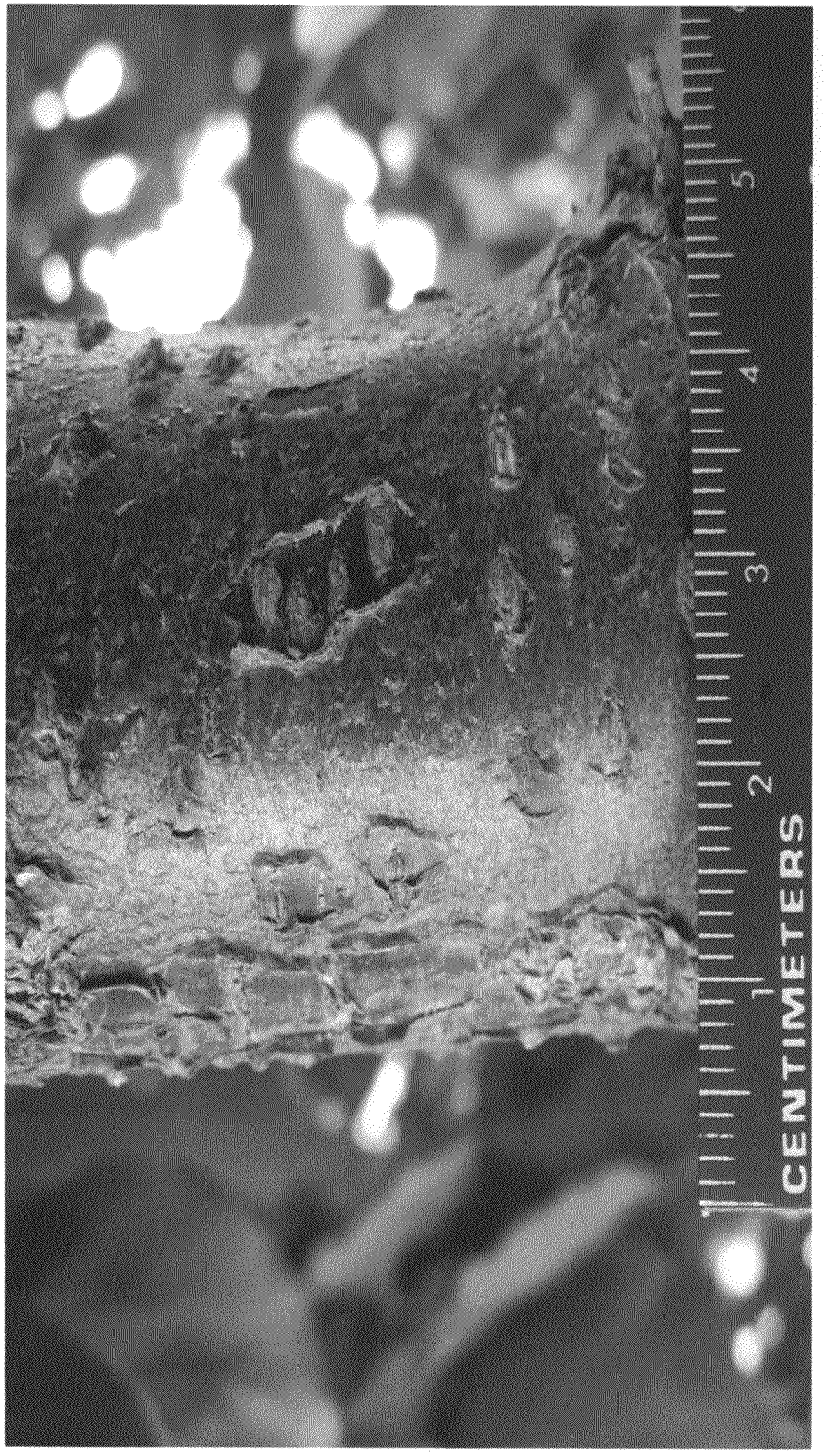
FIG. 2 shows the density and size of lenticles on the bark of the new 'Twocot' apricot.

*Lenticles*.—Prominent and of average density on branches (FIG. 2).

*Shoot color of current season's growth during growing season*.—(0.5-1.5 cm diameter shoots).

Figure 3:
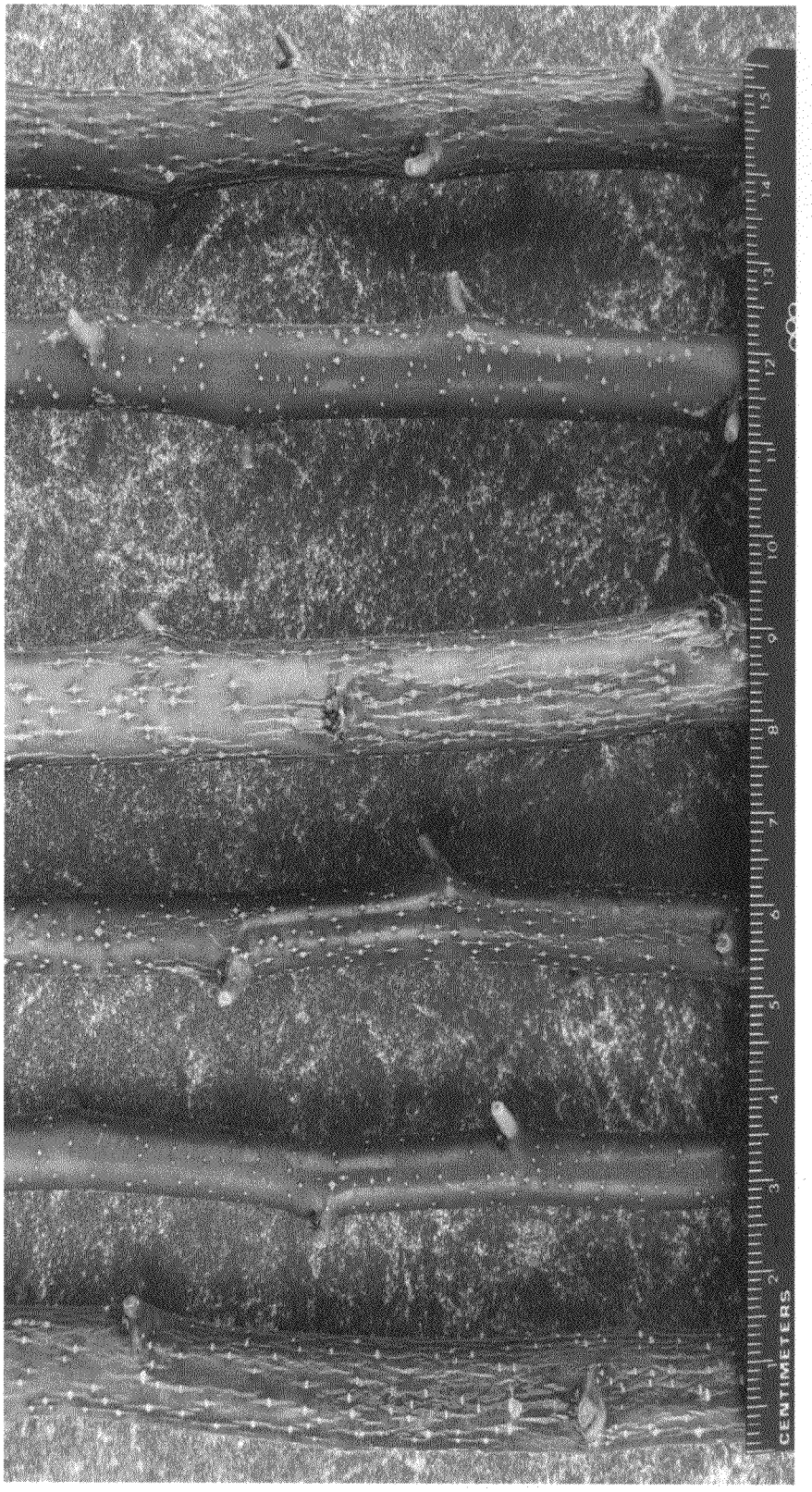
FIG. 3 shows the wide variation in mid-shoot stem color of 'Twocot' apricot as dependent on growth location and sun exposure

*Mid-shoot*.—Varies widely depending on location within tree canopy and sun exposure (FIG. 3). Sun exposed color: Greyed-red (Fan 4, No. 181, B); Sun shaded color: Yellow-green (Fan 3, No. 152, B).

*Shoot terminals*.—Strongly red tinged. Red (Fan 1, No. 46, A).

Leaves: (measurements taken from 25 fully mature leaves of current season growth on shoots randomly selected from seven grafted trees.):

*Size*.—Leaf area: 50.57±9.31 $cm^2$, ranging from 34.6 $cm^2$ to 76.4 $cm^2$. Blade length: 10.13±0.75 cm, ranging from 8.5 cm to 11.7 cm. Blade width: 4.97±0.62 cm, ranging from 3.8 cm to 6.5 cm. Blade thickness: 0.30±0.04 mm, ranging from 0.23 mm to 0.36 mm. Petiole length: 3.94±0.41 cm, ranging from 3.1 cm to 4.7 cm. Petiole width: 1.93±0.16 mm, ranging from 1.57 mm to 2.27 mm.

*Form*.—Cordate.

*Apex*.—Moderately obtuse.

*Base*.—Obtuse.

*Texture*.—Smooth.

*Type*.—Biserrate.

*Serrations*.—Average of 6.3±0.7 serrations/cm as measured at mid-blade.

*Color*.—Upper surface: Luminosity=39.16±1.61, Chroma=22.83±2.60, Hue=125.36±1.19. Lower surface: Luminosity=48.15±1.75, Chroma=21.97±1.65, Hue=123.58±0.88. Stipules: Present at leaf axes of new growth, caducous as leaves reach maturity.

*Glands*.—Location and number varies substantially among leaves, ranging from 1 to 5 globular glands per petiole. Average: 2.48±0.87.

Flowers:

*Flower buds*.—(Evaluated one day pre-anthesis).

*Size*.—approx. 21.7 mm in total length and approx. 11.0 mm in diameter at top of sepal whorl.

*Form*.—Plump.

*Hardiness*.—Abundant flowering in trees grown in the Central San Joaquin Valley, Calif. Winter kill of flower buds has not been observed in Parlier, Calif.

Figure 4:
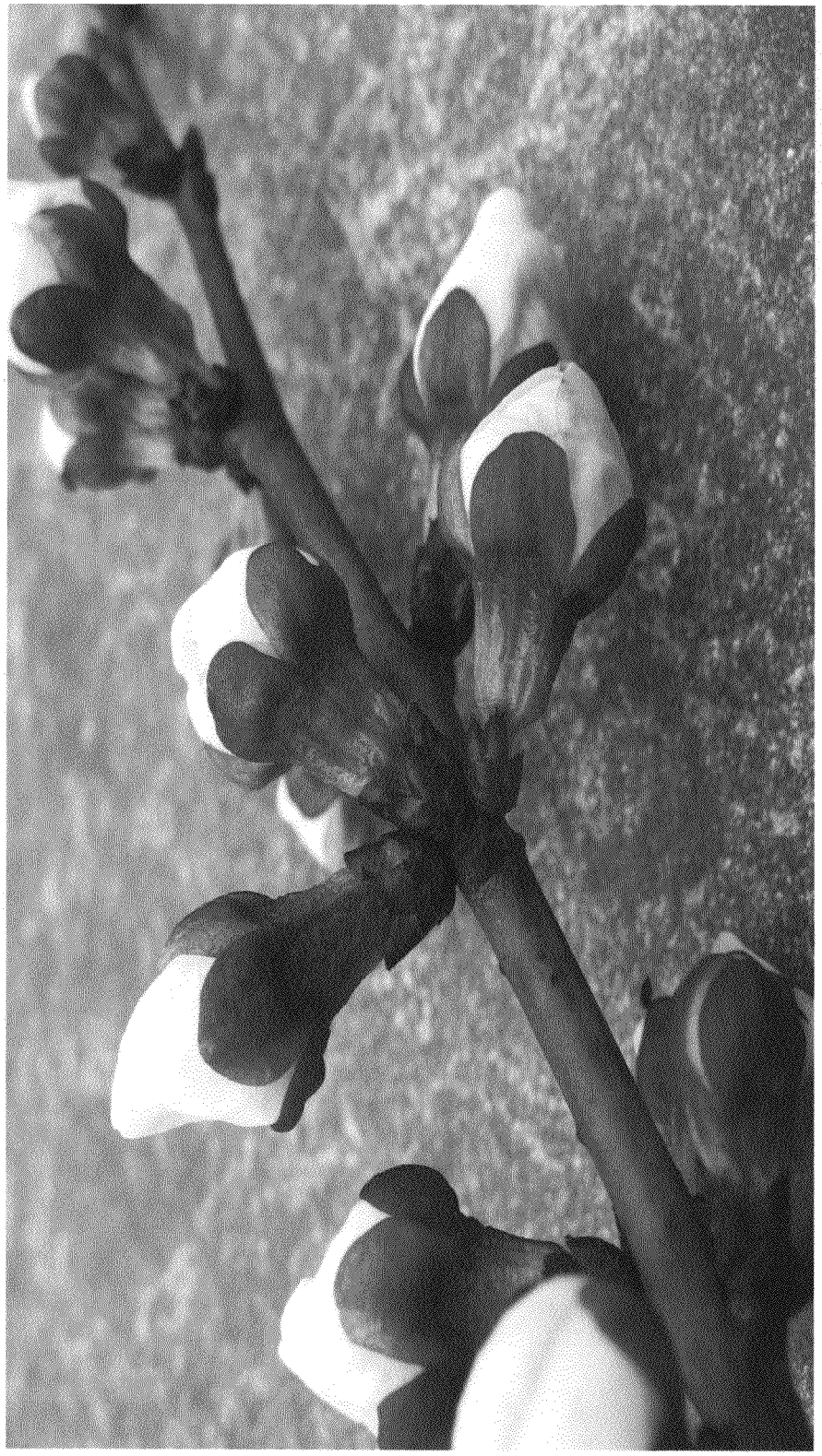
FIG. 4 shows a close-up view of a 'Twocot' fruiting shoot with numerous flower buds on the day prior to anthesis. The photograph demonstrates general petal color at this phenological stage of bloom.
Figure 5:
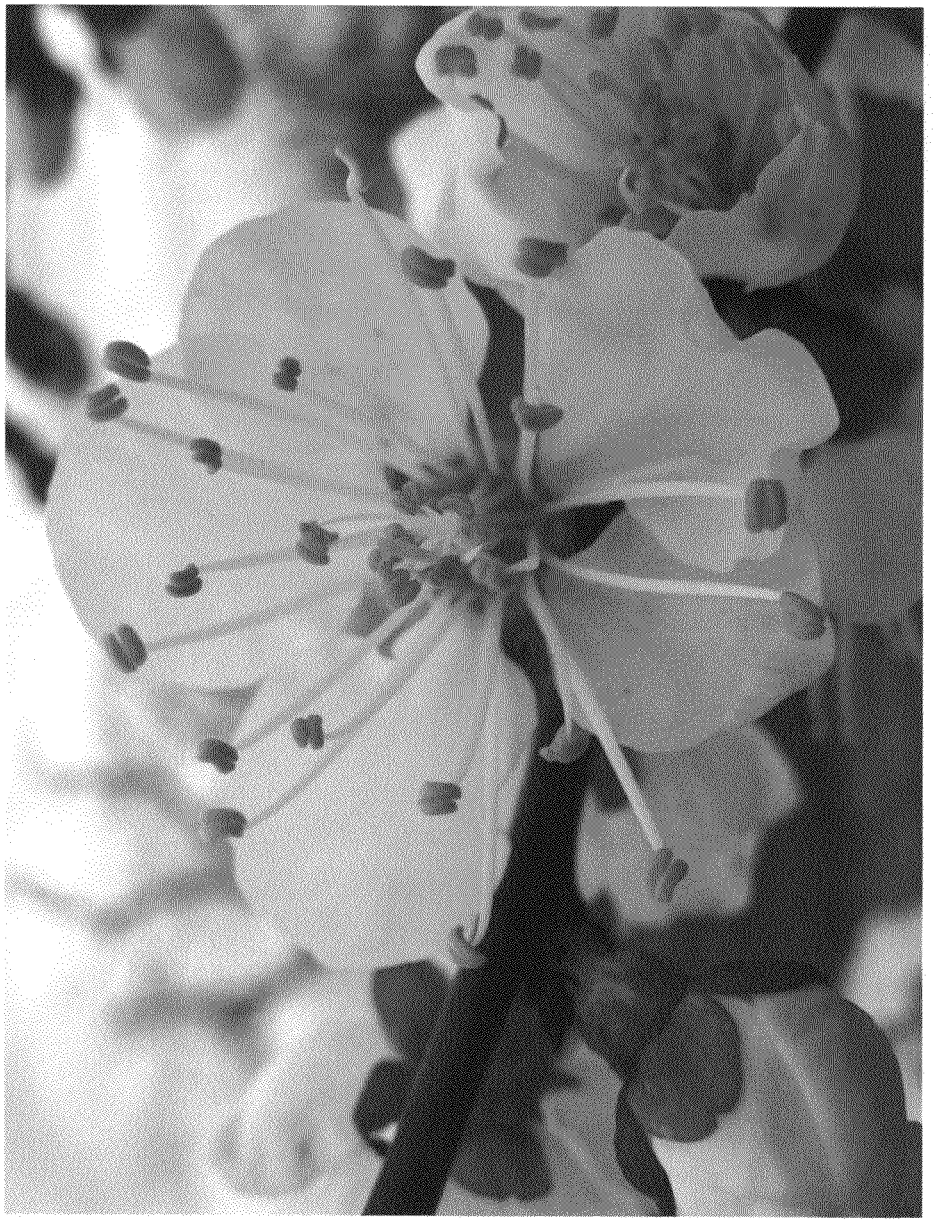
FIG. 5 shows a close-up view of a 'Twocot' flower on the day of anthesis. The photo demonstrates the number of anthers and the faint color sometimes present on the petal margin.

*Petal color*.—White (Fan 4, No. 155, D) with faint red sometimes present on petal margin. (FIG. 4, FIG. 5)

*Flower bud number per node on one-year old shoots*.—1-6 can be present with usually no more than 2 coming to maturity.

*Flower bud number per node on spurs*.—Generally one to three.

*Blooming period*.—Generally a later-blooming variety in relation to the range of bloom dates for other commercial apricot varieties grown in the San Joaquin Valley, Calif. Varies slightly with climactic conditions. Onset of bloom in 2013 on 4 March; full bloom on 13 March; petal fall on 17 March. Of commercial cultivars available in California's San Joaquin Valley, bloom overlap was best with 'Robada' cultivar. Bloom interval (first bloom to full bloom) synchronization with 'Robada' apricot from 2004 through 2011 is shown (FIG. 6).

*Aroma*.—mild to normal aroma.

*Size*.—(At full expansion on day of anthesis).

*Petal whorl diameter*.—38.14 mm.

*Petal length*.—14.4 mm.

*Petal width*.—13.9 mm.

*Petal length*.—Width ratio: average of 1.04, ranging from 0.84-1.23.

*Petal number*.—5.

*Petal shape*.—Generally circular.

*Petal apex shape*.—Rounded.

*Petal margin*.—Entire.

*Petal color*.—White (Fan 4, No. 155, D).

*Sepal number*.—5 fused.

*Sepal apex shape*.—Obtuse (FIG. 4).

*Sepal color*.—Red (Fan 1, No. 45, D).

*Pollen*.—Abundant and self-incompatible.

*Pollen color*.—(Evaluated after screening and drying pollen) yellow-orange (Fan 1, No. 16, B).

*Stamens*.—Number per flower: generally 30, ranging from 28-32 (FIG. 5). Average filament length: 12.6 mm.

*Pistils*.—Number per flower: Usually one. Average pistil length: 19.98 mm. Pistil color: yellow-green (Fan 3, No. 153, D). Pistil pubescence: Present.

Fruit: Data taken from firm-ripe fruit managed to obtain maximum fruit quality.

*Fruit harvest*.—Date of first pick: 7 Jun. 2010. Date of last pick: 17 Jun. 2010.

*Fruit size*.—Average length (stem to apex): 57.2±2.5 mm. Average diameter (in suture plane): 55.9±2.3 mm. Average diameter (perpendicular to suture plane): 56.4±2.2 mm. Average fresh weight: 90.4±10.1 g. Flesh: pit ratio: Approximately 43:1.

*Fruit form*.—Viewed from apex: round (FIG. 7). Viewed from side, perpendicular to suture plane: oblong to elliptic (FIG. 8). Viewed from side, in suture plane: irregularly rounded (FIG. 9). Fruit apex shape: rounded, slightly indented with no sharp point, generally symmetrical halves (FIG. 10). Fruit stem-end cavity depth: slightly depressed in plane of suture.

*Fruit surface*.—Skin thickness: normal thickness. Surface texture: smooth to slightly bumpy. Tenacity: tenacious to flesh. Pubescence: present in normal amount. Ground color: Luminosity=57.4±1.6, Chroma=39.3±3.5, Hue=72.1±3.3. Overcolor: Luminosity=44.9±3.0, Chroma=38.1±3.5, Hue=40.2±6.1. Skin taste: slightly acidic, no astringency noted on skin with strong overcolor. Suture: Shallow and discrete, stitching is uncommon. More prominent at stem end where groove depth can reach 4 mm. (FIG. 10).

*Fruit flesh*.—Ripening character: ripens evenly. Texture: firm and fine with copious juice. Fibers: coarse fibers detected occasionally. Flavor: pleasant sweet-acid mix. Aroma: abundance of aroma increases with fruit ripeness. Brix: Brix increases as flesh firmness decreases (FIG. 11). Acidity: Acidity decreases as flesh firmness decreases (FIG. 12). Color: Luminosity=54.5±1.6, Chroma=43.7±2.1, Hue=68.0±1.9. Eating quality: high.

*Fruit pit*.—Cavity color: slightly darker than surrounding flesh, greyed-orange (Fan 4, No. 164, C) (FIG. 13). Cavity length: 26.7±2.4 mm. Cavity diameter in line with suture plane: 19.7±1.3 mm. Cavity diameter perpendicular with suture plane: 15.0±1.4 mm.

Stone: Measurements were taken on air-dried stones.

*Freeness*.—Botanically freestone, with a slight attachment of the stone along suture (FIG. 7).

*Shape* (*lateral view*).—Ovate (FIG. 14).

*Length*.—25.8±1.2 mm.

*Diameter in suture plane*.—19.8±0.8 mm.

*Diameter perpendicular to suture plane*.—13.2±1.0 mm.

*Form* (*viewed perpendicular to suture*).—Oval.

*Form* (*viewed from stem end*).—Compressed oval.

*Surface color*.—Luminosity=53.4±1.7, Chroma 25.5±1.4, Hue=73.4±1.0.

*Surface characteristics*.—Overall surface is slightly rough and bumpy. No pitting.

*Ridges*.—Present and generally symmetrical, not prominent.

*Tendency to split*.—Stones typically do not split.

*Kernel*.—Taste: sweet, amygdalin not detectable by taste. Viability: viable. Length: 16.9±0.8 mm. Width: 10.5±0.6 mm. Thickness: 6.1±0.5 mm. Pellicle color (when fresh, air dried): Luminosity=57.9±2.0, Chroma=31.9±1.4, Hue=70.4±1.3. Rate of double kernels: Low, less than 10%.

Fruit use: Predominantly for fresh marketing purposes, however, sulfur/sun-dried fruit produce a high quality product.

Fruit shipping/keeping quality: Fresh fruit picked at commercial level of maturity maintain acceptable fruit quality for three weeks in cold storage. Properly sulfured dry fruit halves maintain good color during storage.

We claim:

1. A new and distinct variety of apricot tree, substantially as illustrated and described, characterized by its vigorous vegetative growth on upright to slightly spreading tree form, consistent and productive bearer of medium-sized, freestone fruit with white flesh, self-incompatible flowers that bloom late relative to other apricot cultivars, mature fruit that are aromatic with an attractive skin blush on sun-exposed surfaces, hanging well on a tree after maturity and mid-season fruit harvest.

* * * * *